(12) United States Patent
Välimaa et al.

(10) Patent No.: US 6,524,345 B1
(45) Date of Patent: Feb. 25, 2003

(54) SURGICAL IMPLANT

(75) Inventors: Tero Välimaa, Tampere (FI); Pertti Törmälä, Tampere (FI)

(73) Assignee: Bionx Implants Oy, Tampere (FI)

( * ) Notice: Subject to any disclaimer, the term of this patent is extended or adjusted under 35 U.S.C. 154(b) by 0 days.

(21) Appl. No.: 09/284,803

(22) PCT Filed: Oct. 22, 1997

(86) PCT No.: PCT/IB97/01321
§ 371 (c)(1),
(2), (4) Date: Jul. 21, 1999

(87) PCT Pub. No.: WO98/18408
PCT Pub. Date: May 7, 1998

(30) Foreign Application Priority Data

Oct. 25, 1996 (FI) .................................................. 964323

(51) Int. Cl.7 ............................... A61F 2/28; A61F 2/02
(52) U.S. Cl. ............................... 623/23.56; 623/23.58; 623/23.75
(58) Field of Search ............................... 623/1.38, 1.49, 623/13.18, 23.56, 23.58, 23.72, 23.75

(56) References Cited

U.S. PATENT DOCUMENTS

| | | | |
|---|---|---|---|
| 3,108,357 A | | 10/1963 | Liebig |
| 3,155,095 A | | 11/1964 | Brown |
| 3,272,204 A | | 9/1966 | Artandi et al. |
| 3,463,158 A | | 8/1969 | Schmitt et al. |
| 3,620,218 A | | 11/1971 | Schmitt et al. |
| 4,085,629 A | | 4/1978 | Fogarollo |
| 4,202,055 A | * | 5/1980 | Reiner et al. ............. 623/23.57 |
| 4,435,590 A | | 3/1984 | Shalaby et al. |
| 4,441,496 A | | 4/1984 | Shalaby et al. |
| 4,532,928 A | | 8/1985 | Bezwada et al. |
| 4,559,945 A | | 12/1985 | Koelmel et al. |
| 4,605,730 A | | 8/1986 | Shalaby et al |
| 4,649,921 A | | 3/1987 | Koelmel et al. |
| 4,653,497 A | | 3/1987 | Bezwada et al. |
| 4,700,704 A | | 10/1987 | Jamiolkowski et al. . |
| 4,743,257 A | | 5/1988 | Tormala et al. |
| 4,768,507 A | | 9/1988 | Fischell et al. |
| 4,781,183 A | * | 11/1988 | Casey et al. ............. 623/23.58 |
| 4,923,470 A | | 5/1990 | Dumican |
| 4,950,258 A | | 8/1990 | Kawai et al. |
| 4,973,301 A | | 11/1990 | Nissenkorn |
| 4,990,131 A | | 2/1991 | Dardik et al. |
| 4,994,066 A | | 2/1991 | Voss |
| 5,019,090 A | | 5/1991 | Pinchuk |
| 5,092,890 A | * | 3/1992 | Pohlemann et al. ........ 424/423 |
| 5,160,341 A | | 11/1992 | Brenneman et al. |
| 5,569,264 A | * | 10/1996 | Tamminmaki et al. ...... 606/104 |

FOREIGN PATENT DOCUMENTS

| | | |
|---|---|---|
| DE | 34 21 155 | 12/1985 |
| EP | 0 519 293 | 12/1992 |
| EP | 0606165 | 7/1994 |
| EP | 0 705 609 | 4/1996 |
| WO | WO 83/03752 | 11/1983 |
| WO | WO 84/03035 | 8/1984 |
| WO | WO90/04982 | 5/1990 |
| WO | WO 90/04982 * | 5/1990 |
| WO | WO 94/15583 | 7/1994 |

OTHER PUBLICATIONS

Van Arsdalen et al., "Ureteral Stenting", Seminars in Urology, vol. II, No. 3 (Aug. 1984), pp. 180–186.

Daniel et al., "An Absorbable Anastomotic Device for Microvascular Surgery: Experimental Studies", Plastic & Reconstructive Surgery, vol. 74, No. 3, Sep. 1984, pp. 329–336.

Rajasubramanian et al., "Fabrication of Resorbable Microporous Intravascular Stents for Gene Therapy Applications", ASAIO Journal, Jul.–Sep. 1994, vol. 40, No. 3, pp. M584–M589.

Vainionpaa, et al., "Surgical Applications of Biodegradable Polymers in Human Tissues", Prog. in Polymer Science, vol. 14, No. 5, 1989, pp. 679–716.

\* cited by examiner

*Primary Examiner*—Paul B. Prebilic
*Assistant Examiner*—Brian E Pellegrino
(74) *Attorney, Agent, or Firm*—Kenyon & Kenyon

(57) ABSTRACT

A surgical implant comprising biodegradable polymer interspersed with ceramic particulate that is visible to radioscopy.

22 Claims, 3 Drawing Sheets

SURGICAL IMPLANT

FIELD OF THE INVENTION

The present invention relates to a surgical implant that comprises a biodegradable polymer and a ceramic that is visible to radioscopy.

DESCRIPTION OF RELATED ART

In surgery, it is known to use at least partly bioabsorbable, elongated, typically tubular, screw-like, thread-like or wire-like surgical implants and devices to support or connect or separate elongated organs, tissues, connective tissues, or their parts from each other. These objects include the skeletal system, various ducts, the intestines, blood vessels, tubes, such as the bronchi, the urinary tracts, the nerves, etc.

In this context, bioabsorbable material refers to a material made of a polymer, copolymer, or a polymer blend whose degradation and/or dissolution in an organism takes place by means of metabolic reactions and/or secretion through the kidneys, lungs, or through the intestines or the skin.

A number of publications describe various tubular screw-like, thread- or wire-like implants and surgical devices to be made of biologically stable or bioabsorbable materials. Implants and devices of this kind are disclosed e.g. in the publications U.S. Pat. Nos. 3,108,357; 3,155,095; 3,272,204; 3,463,158; 3,620,218; WO 83/03752; WO 84/03035; Daniel and Olding, Plast. Rec. Surg. 74 (1984) 329; WO 90/04982; Van Andersdahl et al., Seminars in Urology, Vol. 11 (1984) 180; Raja Subra Manian, ASAI Journal 40 (1994) M584; U.S. Pat. Nos. 4,768,507; 4,923,470; 4,973,301; 4,990,131; 4,994,066; 5,019,090; EPO 606 165 A1, WO 94/15583; U.S. Pat. Nos. 4,950,258; 5,160,341; and 4,085,629; 4,743,257.

Known implants and surgical devices of the above-mentioned or similar type, which are biostable or practically undegradable in tissues, have several disadvantages. Their biostable parts, such as fibers, plastic or metal threadings or rings or tubes or the like, remain in the body even after the organ or tissue has healed, and therefore implants and devices of this kind can later be detrimental to the patient, causing e.g. infections, inflammatory reactions, foreign body reactions, and/or they can release particles or corrosion products or the like, which may further cause harmful reactions in the body.

Many known bioabsorbable implants and surgical devices, e.g. many of those described in the above-mentioned publications as well as those of a corresponding type, do not cause the same kind of long-term complications as biostable implants and surgical devices do, because biodegradable implants and devices are dissolved and degraded biologically in the body, finally leaving the tissues entirely.

A defect with known bioabsorbable implants, however, has been the lack of an effective imaging method. This defect causes problems particularly when there is a need to determine the location of an implant or a device during and after its installation. If visual contact with the area is prevented, the installation can be considerably facilitated with an imaging method, with which the proceeding and installation in its place can be monitored during the operation. These imaging methods may include e.g. radiography, ultrasound, magnetography, computer tomography, gamma radiography, spectroscopy, or the like. It is also very important that the implant stays in its place in the installation object, and with a good imaging method, the position of the implant can be easily determined without surgical measures, such as endoscopy.

BRIEF SUMMARY OF THE INVENTION

Bioabsorbable polymers, however, are poorly or not at all visible with imaging methods presently in use. In the present invention, it was surprisingly found that when a ceramic powder or the like is mixed with an implant or corresponding surgical device made of a bioabsorbable polymer, the implant or device can be made visible by imaging methods used in medicine, utilizing x-rays.

When different amounts of ceramic powder or the like, or combinations thereof, are mixed with an implant or a corresponding surgical device made of a bioabsorbable polymer, the implant or device can, depending on the surrounding tissue, be distinguished sufficiently well with an imaging method. Examples of imaging methods are x-ray, ultrasound, magnetography, computer tomography, gamma radiography, spectroscopy, or the like.

Implants or corresponding surgical devices according to the invention can be made of various bioabsorbable polymers, copolymers, or polymer blends, which have been described in a number of publications, for example in: Vainionpää et al., Prog. Polym. Sci. Vol.14, pp. 697–716 (1989); U.S. Pat. No. 4,700,704 (Jamiolkows and Shalaby); U.S. Pat. No. 4,653,497 (Bezwada, Shalaby and Newman); U.S. Pat. No. 4,649,921 (Koelmel, Jamiolkows and Bezwada); U.S. Pat. No. 4,559,945 (Koelmel and Shalaby); U.S. Pat. No. 4,532,928 (Rezada, Shalaby and Jamiolkows); U.S. Pat. No. 4,605,730 (Shalaby and Jamiolkows); U.S. Pat. No. 4,441,496 (Shalaby and Koelmel); U.S. Pat. No. 4,435,590 (Shalaby and Jamiolkows).

The implants or corresponding surgical devices according to the invention can have a structure which is not reinforced, such as made with melt processing techniques or with solution techniques, or they can be reinforced by using e.g. self-reinforcing or reinforcing with absorbable polymer or ceramic fibers.

The method for manufacturing an implant or a corresponding surgical device according to the invention is based on the fact that ceramic powder or the like is added to the material of the implant or corresponding surgical device to make the implant or corresponding surgical device visible with different imaging methods. Examples of the imaging methods are x-ray, ultrasound, magnetography, computer tomography, gamma radiography, spectroscopy, or the like.

In an advantageous embodiment, the implant or corresponding surgical device is manufactured in a way that the quantity of the ceramic powder or the like, added into the polymer, is different in different parts of the implant or corresponding surgical device. For example, the quantity of the ceramic powder or the like can be greater at the first end than at the second end of the implant or corresponding surgical device. Thus, by this method, the visibility of the implant or corresponding surgical device by the imaging method can be made different at different ends of the implant.

The content of the ceramic powder or the like can gradually decrease in the direction of the longitudinal axis of the implant or corresponding surgical device, or the content of the ceramic powder or the like may be different in the body part as compared with the protruding parts of the implant or corresponding surgical device. Further, ceramic powder or the like can be present only in a certain part or location of the implant or corresponding surgical device in a way that there is no ceramic powder or the like in the other parts of the implant or corresponding surgical device at all. By this method, it is possible to manufacture implants or corresponding surgical devices whose visibility with an imaging method is different in different parts of the implant.

The quantity of the ceramic powder or the like can decrease gradually in the direction of the transverse axis of the implant. In this way it is possible to manufacture implants or corresponding surgical devices whose visibility with imaging methods is different in the central part than in the outer shell of the piece.

The invention will become apparent from the following description, with reference to the appended figures and drawings presenting some examples on implants or corresponding surgical devices according to the invention, as well as on applications on methods for their manufacture.

DETAILED DESCRIPTION OF PREFERRED EMBODIMENTS OF THE INVENTION

EXAMPLE 1

A blank having the thickness of 1.1 mm diameter was made of commercial polylactide (manufactured by Purac biochem by., Holland) and commercial barium sulphate ($BaSO_4$ by Merck Ltd., Germany) by extrusion (single-screw extruder) and cooled to room temperature on a moving wire. Barium sulphate was mixed with the polylactide, 30 wt-% in comparison with the mass of the polylactide. The blank was drawn after the first wire through four ovens, between which the speed of the draw belts was accelerated when approaching the fourth oven so that the speed difference between the first and last draw belts was eight times. The temperature of the ovens was 140° C. After the fourth oven, the blank was coiled on a roll with a 100 mm diameter. The yield was a 0.4 mm thick oriented polylactide fiber containing 30 wt-% barium sulphate.

Figure 7:
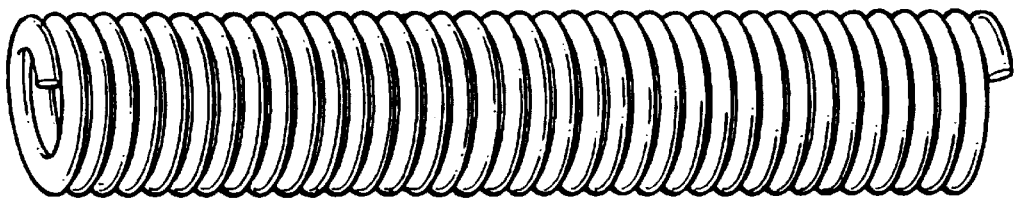
FIG. 7 A view on the model piece for the stents used in Examples 1 and 4.

The blanks were twisted round a rod with a 2.5 mm diameter in the shape shown in FIG. 7 by heating the blanks with a heat blower during the twisting. The spirals (stents) were heated for 10 minutes on moulds at 100° C. temperature in a recirculated air heating chamber, after the moulds had cooled down, the spirals (stents) could be removed from the mould. The stents were packed in a Aluminium-PET foil pouch and gamma sterilized.

As comparison materials, stents made purely of polylactide as well as stents made of polylactide mixed with 10 wt-% barium sulphate were used. These stents were extruded and drawn as well as gamma sterilized in the same way as the polylactide stents containing 30 wt-% barium sulphate described above.

Figure 1:
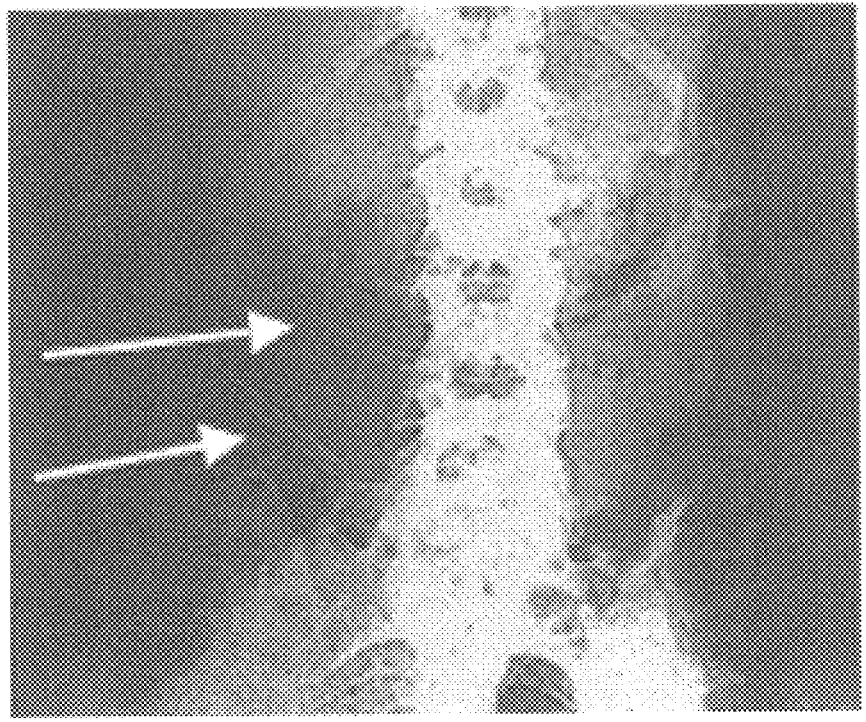
FIG. 1 X-ray illustration on the abdominal area of a test person. Three stents were placed under the test person on the x-ray table. Seen in the direction from the foot end, there were stents containing 30 wt-% and 10 wt-% barium sulphate, respectively, and an unmixed polylactide stent uppermost.
Figure 4:
FIG. 4 An electron microscopic view of the surface of a polylactide fiber mixed with 30 wt-% barium sulphate, showing the barium sulphate nonuniformly interspersed, in a 1000× enlarged view.

The stents containing 30 wt-% barium sulphate and the stents made of the comparison material were placed under the back of a volunteer on an x-ray table. The stents were in the order 30 wt-%, 10 wt-% and unmixed polylactide, seen from the foot end of the test person. Radiography was performed on the abdominal area of the test person. From FIG. 1 it clan be clearly seen how visible the stent containing 30 wt-% barium sulphate is even when radiographed through a test person. The spiral structure of the stent is clearly seen in the figure (lowermost stem). The stent containing 10 wt-% barium sulphate is visible above the stent containing 30 wt-% in the radiograph. The stent containing 10 wt-% barium sulphate is visible in the figure, but its spiral structure cannot be seen. The stent containing only polylactide cannot be seen at all in the radiograph.

EXAMPLE 2

A blank having the thickness of 1.7 mm diameter was made of commercial polyglycolid (Purac biochem by., Holland) by extrusion (single screw extruder) and cooled down to room temperature on a moving wire. The blank was cut into rods of 1 m length. The blanks were drawn at 180° C. temperature into an oriented blank with a draw-down ratio 4, yielding oriented polyglycolid blanks with 0.8 mm thickness. The drawn blanks were cut into lengths of 0.6 meters, and both ends of the lengths were sintered with commercial tricalcium phosphate ($Ca_3O_8P_2$, Merck Ltd., Germany) in an area of 10 cm from the end of the blank. In an assay, the content of tricalcium phosphate was 40 wt-% of the content of polyglycolid in the sintered area.

Figure 2:
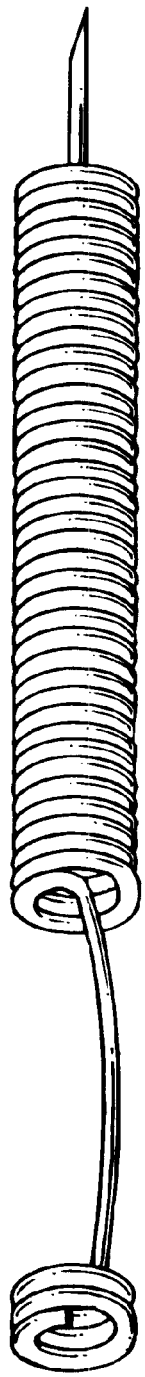
FIG. 2 A spiral (stem) according to Example 2 in a perspective schematic view.

The blanks were twisted to the shape of FIG. 2 around a rod with a 3 mm diameter by heating the blanks with a heat blower during twisting. The ends sintered with tricalcium phosphate were left at both ends of the twisted spiral (stent). The spirals (stents) were heated for 10 minutes on moulds at 100° C. temperature in a recirculated air heating chamber. After the moulds-had cooled down, the spirals (stems) could be removed from the moulds. The stents were packed in an Aluminium-PET foil pouch and sterilized with ethylene oxide gas.

As comparison materials, stents made purely of polyglycolid as well as stents made of blanks having ends sintered with 20 wt-% tricalcium phosphate in the mass of polyglycolid, were used. These stents were extruded and drawn as well as sterilized with ethylene oxide gas in the same way as the above-mentioned polyglycolid stents containing 40 wt-% tricalcium phosphate in a range of 10 cm at both ends.

Figure 5:
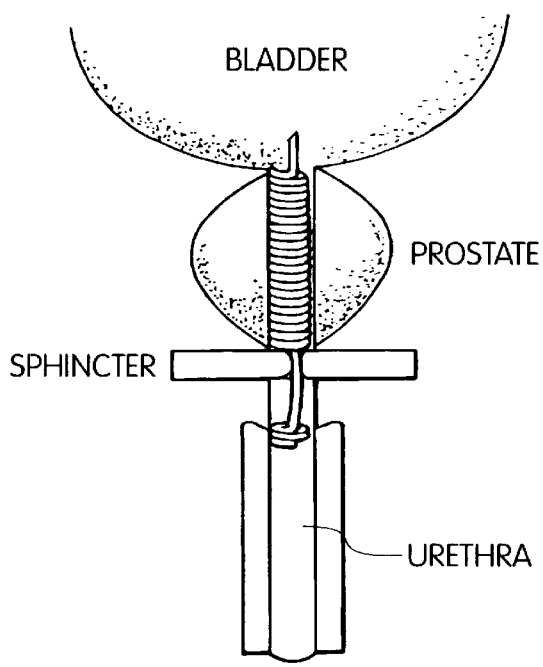
FIG. 5 A schematic view on the spiral according to Example 2, installed in the area of the prostate of a test animal.

The prepared stents were implanted in dog urethras in the area of the prostate in a way that one end of the stents was at the cervix of the urinary bladder and the other end at the urethra side of the sphincter as shown in FIG. 5, and the prostate area of the test animals was radiographed.

The radiographs showed clearly the ends of the stents that contained 40 wt-% tricalcium phosphate at both ends. Also the spiral structure of the stent was shown in the parts where the sintered portion was extended. The unsintered part of the stent was not visible in the radiographs. The stents having ends sintered with 20 wt-% tricalcium phosphate were visible for the ends in the radiographs. However, the spiral structure of these stents was not apparent. The unsintered parts of these stents, and the stents containing only polyglycolid, were not visible in the radiographs.

EXAMPLE 3

Figure 3:
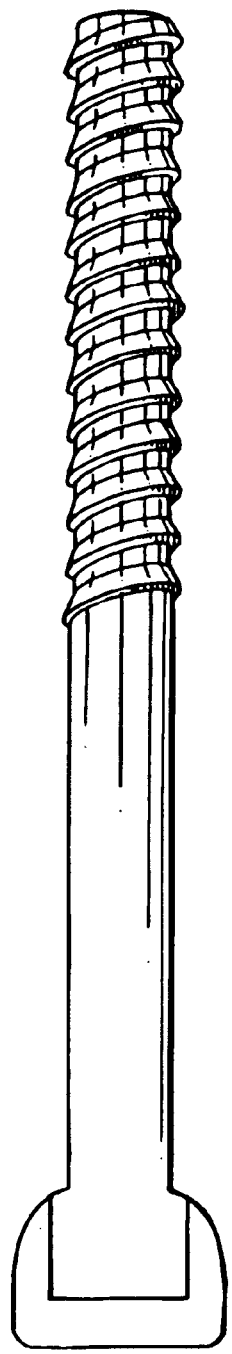
FIG. 3 An implant according to Example 3 in a perspective schematic view.

Screw implants shown in FIG. 3 (diameter 2 mm, length 20 mm) were made from a commercial lactide and trimethylene carbonate copolymer (PLA/TMC manufactured by Boehringer Ingelheim, Germany) and calcium iodapate by the injection molding technique in a way that by adjusting the material extrusion rate and pressure, the highest calcium iodapate density was obtained in the core part and the lowest density on the outer surface of the screw implant. An assay of the implant showed a calcium iodapate density of 40 wt-% in the core and 15 wt-% on the surface of the implant (40/15 wt-%) as compared with the mass of the PLA/TMC. The calcium iodapate content decreased gradually in the direction of the transverse axis of the implant, from the core towards the outer layer. The implants were packed in an Aluminium-PET foil pouch and gamma sterilized.

As comparison materials, implants made purely of PLA/TMC as well as implants made of PLA/TMC with calcium iodapate 20 wt-% in the core and 2 wt-% on the surface (20/2 wt-%) were used. These implants were injection molded and gamma sterilized in the same way as the above-mentioned PLA/TMC implants containing 40/15 wt-% calcium iodapate.

The mixed and unmixed PLA/TMC implants were implanted in the femurs of swines that were used as test animals. Radiography that was performed in the area of installation of the implants did not show the implants made of pure PLA/TMC at all. The implants that were mixed with 20/2 wt-% calcium iodapate were shown in the radiographs as a faint stripe in the bone tissue. The shape of the implant could not be seen. The implants that were mixed with 40/15 wt-% calcium iodapate, were clearly seen in the radiographs so that the core of the implant was clearly apparent and the base part and the spiral part of the implant were slightly less distinguished in the radiographs.

EXAMPLE 4

Several implants (stents) according to Example 1 were prepared, containing 10 wt-%, 30 wt-% and 50 wt-% barium sulphate as compared with the mass of polylactide. The stents were sterilized with gamma radiation. As comparison material, stents made of pure polylactide were used. The stents were installed in surface veins, biliary tracts and femurs of swines that were used as test animals. The stent installation areas were radiographed.

In the area of the surface veins, all the stents containing barium sulphate were clearly visible, and their spiral structure was clearly distinguishable. The stents containing only polylactide were poorly visible in radiographs on the surface veins, and the spiral structure was not distinguishable.

The stents containing 30 wt-% and 50 wt-% barium sulphate and installed in the biliary tracts were clearly visible in the radiographs. Also the spiral structure of the stent was clearly distinguishable. The stents containing 10 wt-% in the biliary tract were visible in the radiograph, but the spiral structure was not apparent. The stents containing polylactide only, installed in the biliary tract, were not visible in the radiographs.

The stents containing 50 wt-% barium sulphate, installed in the femurs, were clearly distinguished from the bone tissue, and the spiral structure was clearly visible. The stents with a 30 wt-% content, installed in the same area, were visible in the radiograph but the spiral structure was not distinguishable. The stents containing 10 wt-% barium sulphate and only polylactide, installed in the femur, were not visible in the radiographs.

EXAMPLE 5

Commercial L-lactide and D-lactide copolymer (poly-L,D-lactide, manufactured by Purac biochem by., Holland) and commercial calcium nitride ($Ca_3N_2$, Tamro Oy), were used to prepare by extrusion (single screw extuder) a blank with a diameter of 4 mm, which was cooled down to room temperature on a moving wire. The poly-L,D-lactide was mixed with 50 wt-% of calcium nitride in the mass of the poly-L,D-lactide. The blank was cut into rods of 1 m length. The blanks were drawn at 180° C. temperature into an oriented blank with a draw-down ratio 4, yielding oriented poly-L,D-lactide blanks of 2 mm thickness. The drawn blanks were cut into lengths of 40 mm which were fumed into screw implants as shown in FIG. 3 (diameter 2 mm, length 20 mm). The implants were packed in an Aluminium-PET foil pouch and sterilized with gamma radiation.

The comparison materials used were implants made purely of poly-L,D-lactide as well as implants made of poly-L,D-lactide mixed with 30 wt-% calcium nitride. These implants were injection molded and gamma sterilized in the same way as the above-mentioned poly-L,D-lactide implants containing 50 wt-% calcium nitride.

The mixed and unmixed poly-L,D-lactide implants were installed in the femurs of sheep that were used as test animals. Radiography of the installation area of the implants did not show the implants made of pure poly-L,D-lactide at all. The implants that were mixed with 30 wt-% calcium nitride were weakly visible in the bone tissue. The shape of the implant was not apparent in these radiographs. The implants containing a mixture of 50 wt-% calcium nitride were clearly shown in the radiographs in a way that the base part of the implant as well as also the spiral part were clearly distinguished in the radiographs.

EXAMPLE 6

Figure 6:
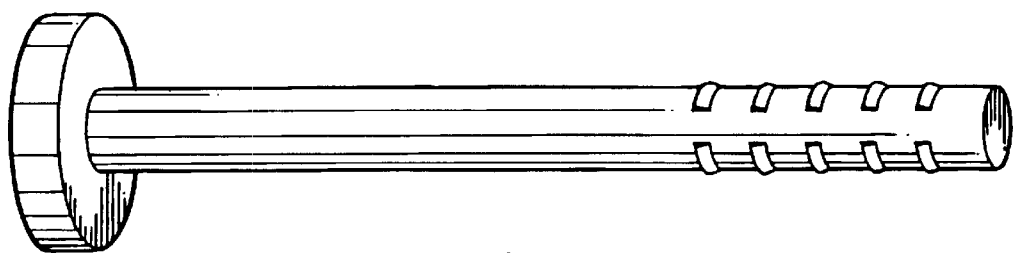
FIG. 6 An implant according to Example 6 in a perspective schematic view.

Commercial poly-L,D-lactide (manufactured by Boehringer Ingelheim, Germany), silicon carbide (a-SiC:H) and zirconium oxide ($ZrO_2$, Merck Ltd, Germany) were used to prepare by extrusion (single-screw extruder) a blank with 3 mm thickness, which was cooled down to room temperature on a movable wire. The poly-L,D-lactide was mixed with 10 wt-% silicon carbide and 20 wt-% zirconium oxide in the mass of the poly-L,D-lactide. The blank was cut into rods of 1 m length. The blanks were drawn at 180° C. temperature into an oriented blank with a drawdown ratio 7, yielding oriented poly-L,D-lactide blanks of 1.1 mm thickness. The drawn blanks were cut into lengths of 10 mm, which were thermoformed into stud implants as shown in FIG. 6 (diameter 1.1 mm, length 10 mm). The implants were packed in an Aluminium-PET foil pouch and sterilized with gamma radiation.

As comparison materials, implants made purely of poly-L,D-lactide as well as implants made of poly-L,D-lactide mixed with 5 wt-% silicon carbide and 10 wt-% zirconium oxide, were used. These implants were extruded, drawn, thermoformed, and gamma sterilized in the same way as the above-mentioned poly-L,D-lactide implants containing 10 wt-% silicon carbide and 20 wt-% zirconium oxide.

The mixed and unmixed implants were used in sheep for testing the fixation of surgically induced rupture of the meniscus. Each implant was tested in two animals. The implants were installed in connection with endoscopy of the meniscus. During the installation, there was direct visual contact with the surgically induced rupture in the meniscus. The implants were triggered with an installation instrument into a preliminary hole made in the tissue of the meniscus. Radiography of the installation area of the implants was performed two days after the installation. The radiography showed clearly the poly-L,D-lactide implants containing 10 wt-% silicon carbide and 20 wt-% zirconium oxide. The implants containing 5 wt-% silicon carbide and 10 wt-% zirconium oxide were slightly visible, and the implants made purely of poly-L,D-lactide were not at all shown in the radiographs.

What is claimed is:

1. A surgical implant, comprising:
    bioabsorable polymeric material; and
    ceramic particulate, wherein said ceramic particulate in said implant is visible to radioscopy, and is nonuniformly interspersed within at least a portion of said polymeric material.

2. The surgical implant of claim 1, wherein a maximum concentration of said ceramic particulate is between 5 to 80 weight percent.

3. The surgical implant of claim 1 wherein said ceramic particulate comprises barium sulphate.

4. The surgical implant of claim 3, wherein the maximum concentration of said barium sulphate is between 10 and 50 weight percent.

5. The surgical implant of claim 1 wherein said ceramic particulate comprises tricalcium phosphate.

6. The surgical implant of claim 5, wherein the maximum concentration of said tricalcium phosphate is between 20 and 40 weight percent.

7. The surgical implant of claim 1 wherein said ceramic particulate comprises calcium iodopate.

8. The surgical implant of claim 7, wherein the maximum concentration of said calcium iodopate is between 15 and 40 weight percent.

9. The surgical implant of claim 1 wherein said ceramic particulate comprises calcium nitride.

10. The surgical implant of claim 9, wherein the maximum concentration of said calcium nitride is between 30 and 50 weight percent.

11. The surgical implant of claim 1 wherein said ceramic particulate comprises silicon carbide.

12. The surgical implant of claim 11, wherein the maximum concentration of said silicon carbide is between 5 and 10 weight percent.

13. The surgical implant of claim 1 wherein said ceramic particulate comprises zirconium oxide.

14. The surgical implant of claim 13, wherein a maximum concentration of said zirconium oxide is between 10 and 20 weight percent.

15. The surgical implant of claim 1, wherein said ceramic particulate comprises a ceramic oxide.

16. The surgical implant of claim 1, wherein said ceramic particulate comprises a ceramic sulphate.

17. The surgical implant of claim 1, wherein said ceramic particulate comprises a ceramic phosphate.

18. The surgical implant of claim 1, wherein said ceramic particulate comprises a ceramic nitride.

19. The surgical implant of claim 1, wherein said ceramic particulate comprises a ceramic carbide.

20. The surgical implant of claim 1, wherein said ceramic particulate comprises a derivative of tri-iodobenzoic acid.

21. The surgical implant of claim 1, wherein the concentration of said ceramic particulate is greater in the interior of said implant than the concentration of said ceramic particulate at the surface of said implant.

22. The surgical implant of claim 1, wherein the concentration of said ceramic particulate is greater either end of said implant than the concentration of said ceramic particulate at the center of said implant.

* * * * *